United States Patent
Mita et al.

(10) Patent No.: US 9,192,514 B2
(45) Date of Patent: Nov. 24, 2015

(54) MEDICAL INSTRUMENT

(71) Applicants: NIDEK CO., LTD., Gamagori-shi, Aichi (JP); RIKEN, Saitama (JP)

(72) Inventors: Osamu Mita, Gamagori (JP); Tsuguo Nanjo, Nagakute (JP); Yoshihisa Harada, Gamagori (JP); Toshifumi Sumiya, Gamagori (JP); Koji Osawa, Gamagori (JP); Susumu Oshima, Gamagori (JP); Masayo Takahashi, Kobe (JP); Hiroyuki Kamao, Kobe (JP)

(73) Assignees: NIDEK CO., LTD., Aichi (JP); RIKEN, Saitama (JP)

( * ) Notice: Subject to any disclaimer, the term of this patent is extended or adjusted under 35 U.S.C. 154(b) by 118 days.

(21) Appl. No.: 13/765,041

(22) Filed: Feb. 12, 2013

(65) Prior Publication Data

US 2013/0218293 A1 Aug. 22, 2013

(30) Foreign Application Priority Data

Feb. 13, 2012 (JP) ................................ 2012-028966

(51) Int. Cl.
  *A61M 5/315* (2006.01)
  *A61F 9/007* (2006.01)
  *A61M 5/178* (2006.01)
  *A61M 1/00* (2006.01)

(52) U.S. Cl.
  CPC .............. *A61F 9/007* (2013.01); *A61M 1/0041* (2013.01); *A61M 5/178* (2013.01); *A61F 9/00727* (2013.01); *A61M 1/0009* (2013.01); *A61M 1/0062* (2013.01); *A61M 5/31511* (2013.01); *A61M 2210/0612* (2013.01)

(58) Field of Classification Search
  CPC ..................... A61M 5/31581; A61M 5/31856; A61M 5/128; A61M 5/322
  USPC .................................................... 604/218, 211
  See application file for complete search history.

(56) References Cited

U.S. PATENT DOCUMENTS

| | | | | | |
|---|---|---|---|---|---|
| 2,725,877 | A | * | 12/1955 | Reiter et al. | 604/135 |
| 3,495,591 | A | * | 2/1970 | Wilson | 604/507 |
| 6,159,218 | A | | 12/2000 | Aramant et al. | |
| 6,235,004 | B1 | * | 5/2001 | Steenfeldt-Jensen et al. | 604/207 |
| 6,641,566 | B2 | * | 11/2003 | Douglas et al. | 604/218 |

FOREIGN PATENT DOCUMENTS

| | | |
|---|---|---|
| JP | 9-501303 A | 2/1997 |
| WO | 9425569 A1 | 11/1994 |

OTHER PUBLICATIONS

Yasuhiko Hirami et al., "Generation of retinal cells from mouse and human induced pluripotent stem cells"; pp. 126-131, Issue 3, vol. 458, Jul. 24, 2009, Neuroscience Letters.

\* cited by examiner

*Primary Examiner* — Edelmira Bosques
(74) *Attorney, Agent, or Firm* — Rankin, Hill & Clark LLP (57) ABSTRACT

A medical instrument includes a handpiece, a tank portion for housing a fluid, a plunger that changes a volume or pressure of an inside of the tank portion to suction the fluid into the tank portion or discharge the fluid from the tank portion, and an operating unit for operating the plunger. The handpiece includes a grip portion at the front end, and an operation member of the operating unit is disposed on a side of the grip portion.

18 Claims, 5 Drawing Sheets

MEDICAL INSTRUMENT

CROSS-REFERENCE TO RELATED APPLICATION

This application is based on Japanese Patent Application No. 2012-28966 filed with the Japan Patent Office on Feb. 13, 2012, the entire content of which is hereby incorporated by reference.

BACKGROUND

1. Technical Field

The present disclosure relates to a medical instrument.

2. Related Art

In recent years, regarding regenerative medicine in the field of ophthalmology, a treatment method including culturing retinal pigment epithelial cells in a sheet shape and implanting the epithelial cells under the retina in the fundus of a patient's eye has been proposed (see JP-A-1997-501303).

Also, according to a technology proposed in recent years, a sheet of retinal pigment epithelial cells as a graft is made by causing cells acquired from the patient or another person (donor) to differentiate into retinal pigment epithelial cells. This technology is discussed by, for example, Y. Hirami, M Takahashi, and six others in "Generation of retinal cells from mouse and human induced pluripotent stem cells", Neuroscience Letters, 2009 Jul. 24, Volume 458, Issue 3, p 126-131.

In the above technologies, it is not easy to perform surgery for transplanting (placing) the prepared transplant under the retina in the fundus of the patient's eye. U.S. Pat. No. 6,159,218 proposes a surgical instrument for facilitating such transplant surgery.

SUMMARY

A medical instrument includes a handpiece, a tank portion configured to house a fluid, a suction/discharge unit configured to change a volume or pressure of an inside of the tank portion to suction the fluid into the tank portion or discharge the fluid from the tank portion, and an operating unit providing a member different from the suction/discharge unit and configured to operate the suction/discharge unit.

DETAILED DESCRIPTION

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the instrument disclosed in U.S. Pat. No. 6,159,218, a predetermined member pushes a graft from the rear of the graft, whereby the graft is pushed out of the instrument. However, when the graft is pushed out of the instrument, the graft and the instrument mechanically contact with each other. Thus, there is a possibility of damaging the graft. It is also difficult to perform the operation for pushing the graft in a suitable manner.

An object of an embodiment of the present disclosure is to provide a medical instrument that is easy to handle, operable with one hand, and easy to operate. Another object is to provide a medical instrument that enables transplantation while preventing the graft from damage.

According to an embodiment of the present disclosure, a medical instrument includes a handpiece; a tank portion configured to house a fluid; a suction/discharge unit configured to change a volume or pressure of an inside of the tank portion to suction the fluid into the tank portion or discharge the fluid from the tank portion; and an operating unit providing a member different from the suction/discharge unit and configured to operate the suction/discharge unit.

The medical instrument can be easily handled. The medical instrument enables a transplantation operation to be performed while preventing the graft from damaging.

In the following, a medical instrument ("the present medical instrument") according to an embodiment of the present disclosure will be described with reference to the drawings. In the following, an ophthalmic surgical instrument will be described as an example of the present medical instrument. The ophthalmic surgical instrument is used for a transplant surgery for transplanting (placing) a graft under the retina in the fundus of the patient's eye. Specifically, the ophthalmic surgical instrument is used for suctioning and holding a graft in the instrument, and discharging (delivering) the graft under the retina.

Figure 1:
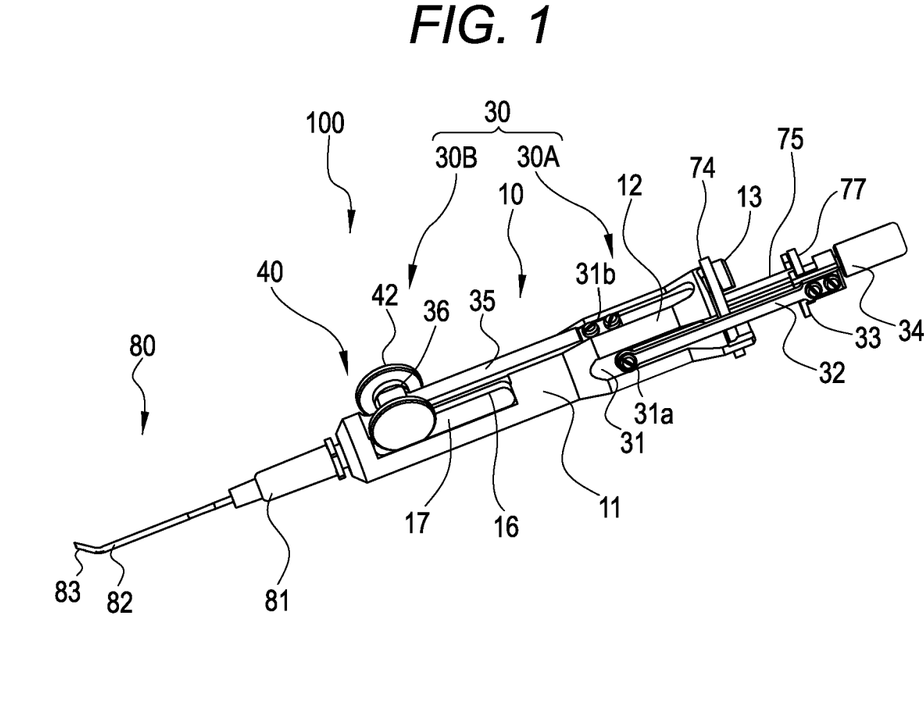
FIG. 1 is an external perspective view of an ophthalmic surgical instrument according to an embodiment of the present disclosure.
Figure 2A:
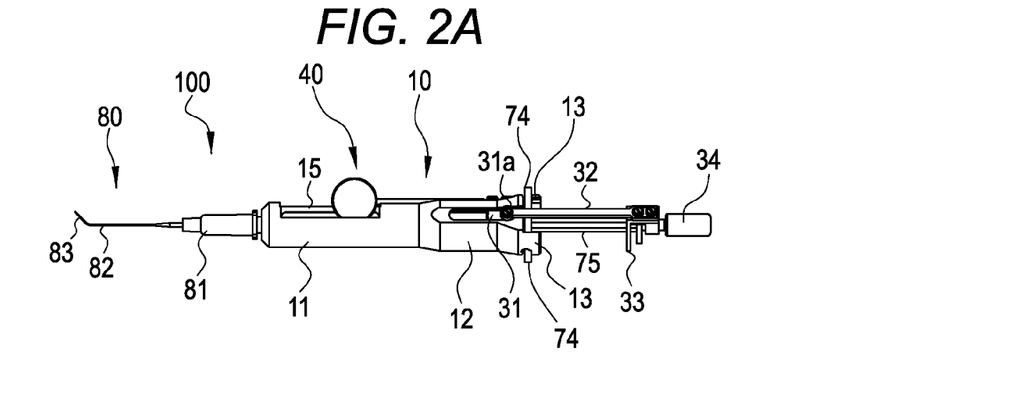
FIGS. 2A to 2C are side views of the ophthalmic surgical instrument.
Figure 2B:
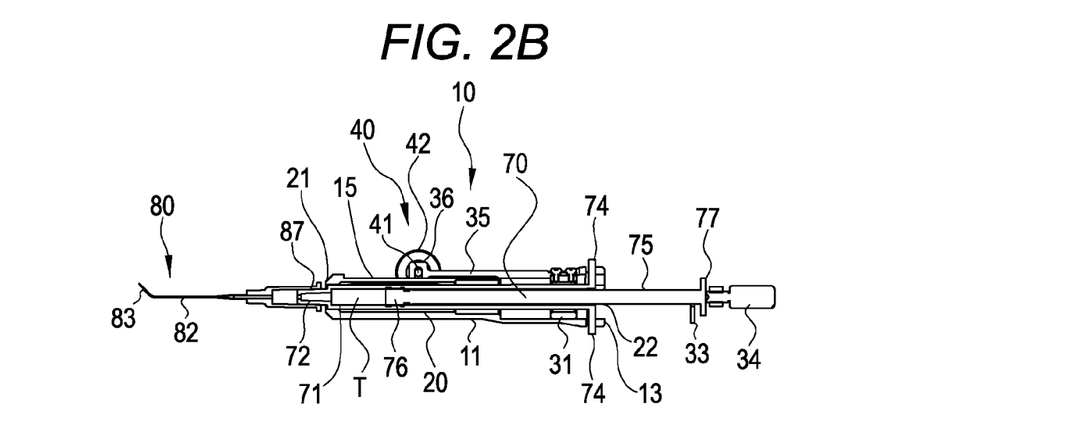
Figure 2C:
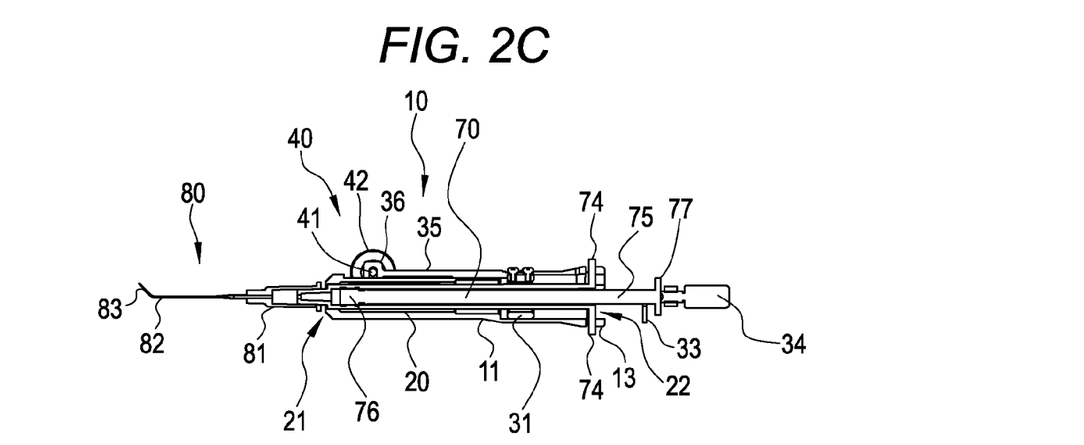

FIG. 1 is an external perspective view of an ophthalmic surgical instrument 100 according to the present embodiment. FIGS. 2A to 2C are side views of the ophthalmic surgical instrument 100.

The ophthalmic surgical instrument 100 (hereafter referred to as a "surgical instrument 100") illustrated in FIG. 1 and FIGS. 2A to 2C includes a handpiece 10 that can be repeatedly used (i.e., of reusable type), and a syringe 70 and a nozzle 80 which are disposable. The handpiece 10 is made of a material adapted for autoclaving and having durability to withstand multiple uses. The handpiece 10 includes components of a corrosion-resistant metal, such as stainless steel or titanium. The syringe 70 may be a disposable (one-use) syringe circulating for medical purposes. The syringe 70 has a volume of 1 mL, for example. The nozzle 80 is made of a material including a resin with biocompatibility. The nozzle 80 has a hollow tubular shape. The nozzle 80 is detachable from the handpiece 10 and may be disposed after a single use. FIG. 2A is a side view of the surgical instrument 100. FIG. 2B is a cross sectional view (lateral cross sectional view) of the surgical instrument 100 along a central axis thereof. FIG. 2C is a lateral cross sectional view of the surgical instrument 100 in a state in which a plunger 75 is moved forward from the state of FIG. 2B.

The syringe 70 is provided with an outer cylinder 71, a front end portion 72, and the plunger (push-out bar) 75 (see FIGS. 2B and 2C). The outer cylinder 71 is a tubular member with an opening in a rear end portion thereof. The outer cylinder 71 is detachable from the handpiece 10. The front end portion 72 is disposed at the front end of the outer cylinder 71 and has an opening. At the rear end portion of the outer cylinder 71, a flange (collar portion) 74 is disposed. The front end portion 72 has an outer diameter smaller than the outer diameter of the outer cylinder 71. The nozzle 80 is mounted on the front end portion 72. In the rear end portion, the plunger 75 is fitted.

At the front end of the plunger 75, an elastic member 76 of rubber, resin and the like is disposed. At the rear end of the plunger 75, a pressing portion 77 is provided. The pressing portion 77 is pressed by a surgeon's finger, for example. The outer shape of the elastic member 76 is slightly larger than the inner diameter of the outer cylinder 71. When the plunger 75 is fitted in the outer cylinder 71, the inside (open portion) of the outer cylinder 71 is hermetically sealed by the elastic member 76. Thus, the space inside the outer cylinder 71 (syringe 70) functions as a tank (tank portion T) for storing a fluid (see FIG. 2B). The plunger 75 is movable in the longitudinal direction of the outer cylinder 71 (axial direction of the syringe 70 and handpiece 10). According to the present embodiment, the front end portion 72 side of the syringe 70 is defined as the "front side" in the longitudinal direction. Thus, the plunger 75 is moved in a front-rear direction.

When the plunger 75 is moved forward, the volume of the tank portion T is decreased. When the plunger 75 is moved backward, the volume of the tank portion T is increased. In the tank portion T, a positive pressure or a negative pressure is produced depending on the change in volume. The plunger 75 functions as a suction/discharge unit for suctioning or discharging the fluid into the tank portion T. As the plunger 75 is moved in the front-rear direction (with the resultant change in volume of the tank portion T), the fluid is suctioned into the tank portion T or the fluid in the tank portion T is discharged via the nozzle 80 and the front end portion 72. According to the present embodiment, the fluid includes an ophthalmic irrigating solution (physiological saline), for example. The fluid may be a viscoelastic substance or an ophthalmic drug.

The handpiece 10 is provided with a grip portion 11, a guide pipe 12, a fixing portion 13, a pipe portion 20, a movable unit 30, and a rotary knob 40. The grip portion (handle portion) 11 forms an outer cylinder of the handpiece 10 that is held by the surgeon's fingers. The guide pipe 12 guides the movement of the movable unit 30. The fixing portion 13 fixes (holds) the syringe 70 onto the handpiece 10. The pipe portion 20 is an inner cylinder configured to house and hold the syringe 70 (or the outer cylinder 71 thereof) in the handpiece 10. The movable unit 30 is a member for moving the plunger 75. The rotary knob 40 is an operating member (operating unit) that the surgeon uses to operate the movable unit 30. The rotary knob 40 forms a part of the movable unit 30.

The grip portion 11 has an outer diameter (size) such that the surgeon can easily hold the grip portion 11 with one hand. In the guide pipe 12, a ring 31 of the movable unit 30 is slidably mounted, as will be described later. The guide pipe 12 has slits at two locations along the axial direction. Via these slits, the ring 31 is connected to a bar 32 and a slide bar 35, as will be described later.

The fixing portion 13 illustrated in FIG. 1 is disposed at the rear end of the handpiece 10. The fixing portion 13 has a guide hole for holding the flange 74. The guide hole is disposed opposite the axis of the pipe portion 20 in such a manner as to correspond to the flange 74. When the outer cylinder 71 of the syringe 70 is put in the pipe portion 20, the flange 74 of the syringe 70 is housed in the guide hole along the axial direction. When the syringe 70 is rotated, the flange 74 is held in the guide hole. Thus, the flange 74 is fixed onto the fixing portion 13 by the guide hole such that the movement of the flange 74 in the front-rear direction is prevented. Accordingly, the outer cylinder 71 is held in the handpiece 10 while being fixed (locked) onto the fixing portion 13 in such a manner as to not move in the front-rear direction. The fixing portion 13 is an attaching/detaching member for detachably fixing the syringe 70 including the tank portion T onto the handpiece 10 (pipe portion 20).

The pipe portion 20 penetrates the handpiece 10 (the grip portion 11 to the fixing portion 13) in the axial direction. The pipe portion 20 has an inner diameter allowing the outer cylinder 71 of the syringe 70 to be housed therein. The inner diameter of the pipe portion 20 is slightly larger than the outer diameter of the outer cylinder 71, for example. Thus, the syringe 70 can be stably held when the outer cylinder 71 is housed in the pipe portion 20. At the front end of the pipe portion 20, an opening 21 for inserting (exposing) the front end portion 72 of the syringe 70 is provided. The diameter of the opening 21 is smaller than the diameter of the outer cylinder 71 and larger than the front end portion 72. The opening 21 has the function of preventing the syringe 70 from being pulled off forward. At the rear end of the fixing portion 13, an opening 22 is formed. The outer cylinder 71 is put in or out through the opening 22.

The movable unit 30 is provided with a holder 30A, the rotary knob 40, and a slider 30B. The holder 30A holds the pressing portion 77 of the plunger 75. The rotary knob 40 is a rotary member operated by the surgeon. As the rotary knob 40 is rotated, the holder 30A is moved.

The holder 30A and the slider 30B commonly utilize the ring 31. The ring 31 is movably disposed in the guide pipe 12. The ring 31 provides a base portion of the movable unit 30. The holder 30A is disposed rearwardly of the ring 31. The slider 30B is disposed forwardly of the ring 31. The holder 30A is provided with the bar 32, a plate 33, and a rotary pin 34. The bar 32 is axially rotatably held onto a pin 31a attached to the ring 31. The plate 33 is disposed at the rear end of the bar 32. The rotary pin 34 fixedly holds the pressing portion 77.

The bar 32 can be rotated from the state illustrated in FIG. 2A, in which the bar 32 is positioned parallel with the plunger 75 (axial direction), in an upper or lower direction with respect to the handpiece 10 about the pin 31a. The plate 33 has an internal thread. The rotary pin 34 has an external thread.

The rotary pin 34 is threadedly engaged with the plate 33. By axially rotating the rotary pin 34, the rotary pin 34 as a whole can be moved in the front-rear direction. As the rotary pin 34 is rotated and moved forward with the pressing portion 77 placed between the plate 33 and the rotary pin 34, the pressing portion 77 is sandwiched between the plate 33 and the rotary pin 34. Thus, the plunger 75 is fixedly held onto the holder 30A.

When removing the plunger 75, the rotary pin 34 is rotated and moved backward. Then, the plate 33 and the bar 32 are rotated in the lower direction. Further, the fixing between the fixing portion 13 and the flange 74 is released. Thereafter, the plunger 75 is removed from the pipe portion 20.

Two bars 32 may be provided, one on a left side and the other on a right side of the pushing shaft. The bar 32 may be formed on only one of the left and right sides. According to the present embodiment, the bar 32 is formed only on the left side with respect to the direction facing the front end. Thus, when the handpiece 10 is held with the right hand, the bar 32 is prevented from easily contacting the fingers and palm of the right hand. Accordingly, an improved operational feeling can be obtained. When the handpiece 10 is to be held with the left hand, the bar 32 may be formed on the opposite side (right side).

The rotary pin 34 has a balancer function for adjusting the position of the center of gravity of the surgical instrument 100. Providing the rotary pin 34 with a certain weight moves the center of gravity of the surgical instrument 100 from the front side to the rear side of the grip portion 11. Preferably, the center of gravity of the surgical instrument 100 is positioned at the center of the surgeon's hand holding the handpiece 10.

The slider (movable member) 30B is provided with the ring 31, the linear slide bar 35, and a hook 36. The slide bar 35 is screwed onto the ring 31 by screws 31b. The hook 36 is disposed at the front end of the slide bar 35. The hook 36 rotatably holds the rotary knob 40. In an upper part of the grip portion 11, a guide rail 15 and wall portions (side walls) 16 are provided. The guide rail (guide portion) 15 guides the movement of the rotary knob 40 (slide bar 35). The wall portions 16 are disposed opposite each other in such a manner as to support the side surfaces of the rotary knob 40. Thus, the plunger 75 is connected to the rotary knob 40 via the holder 30A and the slider 30B.

The rotary knob (operating unit) 40 is a different member from the plunger (suction/discharge unit) 75. In other words, the rotary knob 40 is a separate member from the plunger 75 which is not integrally formed with the plunger 75. The rotary knob 40 is disposed laterally of the plunger 75.

The guide rail 15 and the wall portions 16 have linear shapes extending in the front-rear direction (axial direction). The guide rail 15 and the plunger 75 have different axes. According to the present embodiment, the axis of the guide rail 15 and the axis of the plunger 75 are parallel but not coaxial.

The hook 36 is disposed at the front end of the slide bar 35. The hook 36 is hooked onto a shaft 41 of the rotary knob 40, as will be described later. In other words, the hook 36 is configured to rotate the rotary knob 40. The hook 36 has the function of moving the slide bar 35 in the axial direction by rotating the rotary knob 40.

Figure 3:
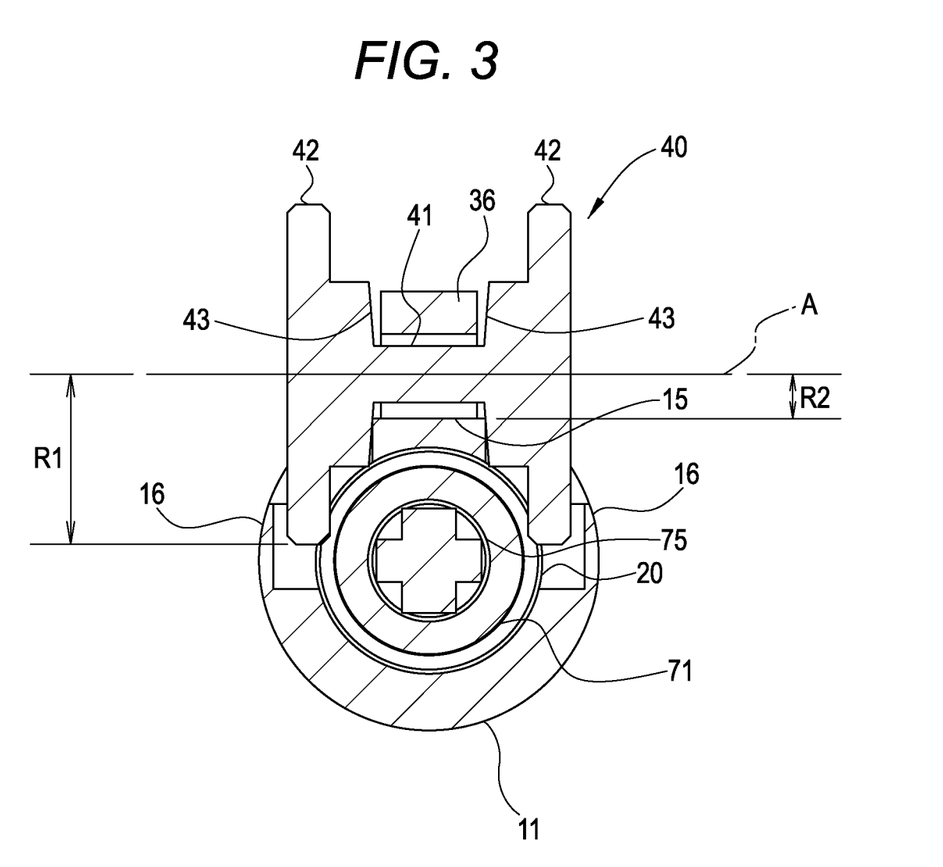
FIG. 3 is a cross sectional view of the ophthalmic surgical instrument in the vicinity of a rotary knob thereof.

FIG. 3 illustrates a configuration of the rotary knob 40. As illustrated in FIG. 3, the rotary knob 40 is provided with the shaft 41, disc portions 42, and sloped portions 43. The disc portions 42 are disposed on both sides of the shaft 41 and have a diameter greater than the shaft 41. The sloped portions 43 are sloped from the shaft 41 toward the outer periphery of the disc portions 42. According to the present embodiment, the rotary knob 40 is an integral member. The peripheral edges of the disc portions 42 are formed with knurls or the like for preventing slippage where the surgeon places his finger. The slip preventing knurls or the like help the surgeon rotate the rotary knob 40. Preferably, at least a part of the rotary knob 40 is exposed (i.e., disposed over the handpiece 10) in such a manner as to facilitate manual operation by the surgeon. The sloped portions 43 are the parts of the disc portions 42 in which the thickness is decreased from the shaft 41 toward the outer periphery of the disc portions 42. In other words, the sloped portions 43 are tapered. The width of the shaft 41 (length of the shaft 41 in the axial direction thereof) is designed such that the shaft 41 does not contact the upper surface of the guide rail 15 when the sloped portions 43 are in contact with the corners of the guide rail 15. Thus, the sloped portions 43 of the rotary knob 40 contact the guide rail 15.

As the disc portions 42 are rotated, the rotary knob 40 is moved along the guide rail 15 and the wall portions 16 in the front-rear direction. In accordance with the movement of the rotary knob 40 in the front-rear direction, the slider 30B (the hook 36, slide bar 35, and ring 31) and the holder 30A (the ring 31, bar 32, plate 33, and rotary pin 34) are integrally moved, whereby the plunger 75 is moved in the front-rear direction. Then, the outer cylinder 71 is fixedly held by the fixing portion 13. Accordingly, the plunger 75 is moved relatively to the outer cylinder 71 in the front-rear direction.

The amount of movement of the rotary knob 40 is proportional to the amount of rotation of the rotary knob 40 (disc portions 42). According to the present embodiment, the guide rail 15 contacts predetermined portions of the rotary knob 40 (sloped portions 43). The diameter of the sloped portions 43 is smaller than the diameter of the disc portions 42, i.e., the maximum outer diameter of the rotary knob 40. Thus, the actual amount of movement of the rotary knob 40 in the front-rear direction is smaller than the amount of rotation of the disc portions 42. As illustrated in FIG. 3, the distance between a rotation axis A of the shaft 41 and the peripheral edge of the disc portions 42 is R1 (which corresponds to one half the maximum outer diameter of the rotary knob 40). The distance between the rotation axis A and the guide rail 15 is R2. Then, the ratio of the amount of movement of the rotary knob 40 in the front-rear direction due to the rotation of the disc portions 42 to the amount of rotation of the disc portions 42 when the disc portions 42 are rotated on a predetermined plane is equal to the ratio of the distance R2 to the distance R1 (R2/R1).

Thus, the amount of rotation of the rotary knob 40 (disc portions 42) is translated into a reduced linear amount of movement (i.e., an amount of rolling of the rotary knob 40) which is transmitted to the slider 30B, the holder 30A, and the plunger 75. Such a mechanism facilitates fine-adjustment of the operation for the fluid in the tank portion T. As a result, a fluid and/or a graft can be suctioned and discharged via the nozzle 80 with improved operability.

As illustrated in FIGS. 2B and 2C, the rotary knob 40 is moved forward by rotating without changing the height position of the rotary knob 40. Then, as the shaft 41 of the rotary knob 40 is moved, members integral with the hook 36 and the slide bar 35 and the like are moved forward. As a result, the plunger 75 is moved forward, whereby the volume of the tank portion T is decreased. At the same time, the fluid in the tank portion T is discharged outside. When the rotating direction of the rotary knob 40 is reversed, the opposite operation results, whereby the fluid can be suctioned (allowed to enter) into the tank portion T.

Preferably, the plunger 75 (elastic member 76) may have a minimum cross sectional area (of the tank portion T) so as to facilitate the adjustment of the volume of the tank portion T. In this way, suctioning and discharging of the fluid can be fine-adjusted more easily.

During the rotation of the rotary knob 40, and when the slide bar 35 is moved in the front-rear direction, the frictional force that acts on the rotary knob 40 and the slide bar 35 is small (i.e., the area of contact of the rotary knob 40 and the slide bar 35 with the other members is small). Thus, the difference between the frictional force acting on the rotary knob 40 and the slide bar 35 immediately before the rotary knob 40 and the slide bar 35 start to move (maximum static frictional force) and the frictional force when the rotary knob 40 and the slide bar 35 are moving (dynamic frictional force) can be decreased. Accordingly, the sense of resistance that the surgeon may feel before and after movement of the rotary knob 40 can be decreased, so that the surgeon can have an improved operational feeling.

Generally, when handling a syringe, the surgeon holds the outer cylinder of the syringe with one hand and then operates the plunger with the other hand. Thus, the both hands are occupied for suctioning and discharging operations by the syringe. This may lead to problems, such as the increase in the need for an assistant during surgery. In contrast, the surgical instrument 100 enables the surgeon to perform suctioning and discharging by the syringe 70 with one hand (i.e., the syringe 70 can be operated with one hand). Accordingly, the surgeon can perform other tasks with the other hand, so that the surgeon can enjoy a significantly increased degree of freedom during surgery, and the need for an assistant is lowered. For example, when transplanting a cell sheet under the retina, the surgeon can perform the suctioning and discharging (injection) by the surgical instrument 100 with one hand while holding a light guide with the other hand. In this way, the surgeon can perform the surgery without an assistant.

Figure 4:
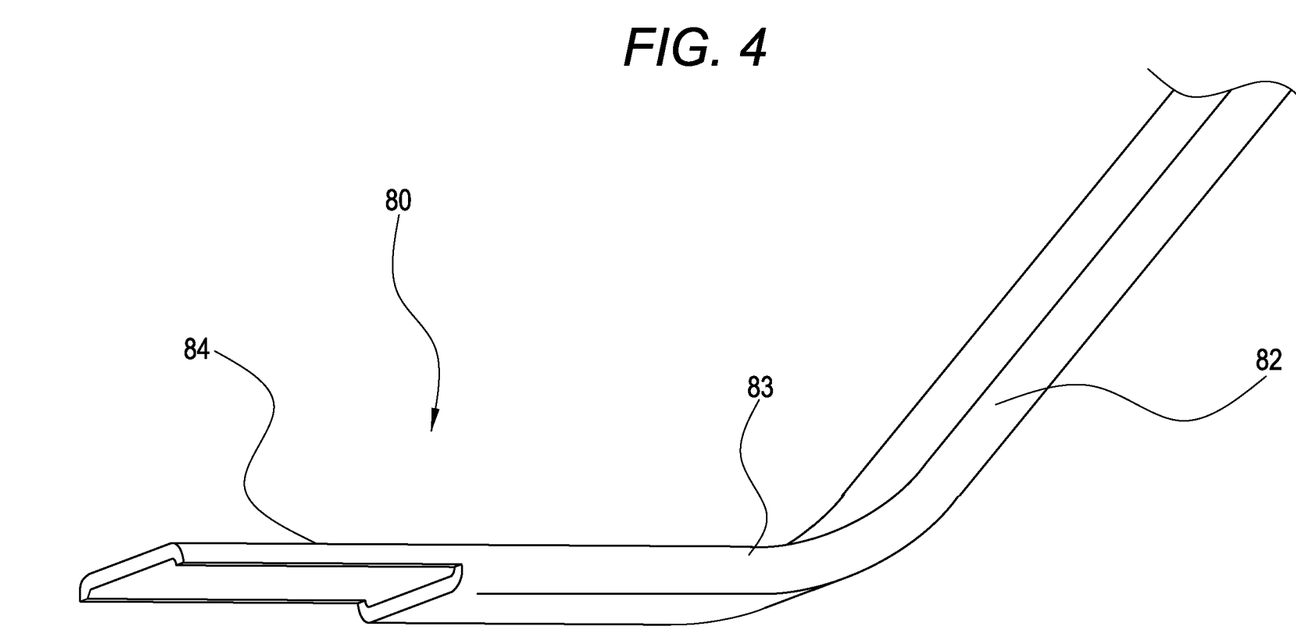
FIG. 4 is an enlarged perspective view of a nozzle in the vicinity of a front end thereof.

FIG. 4 is an enlarged perspective view of the nozzle 80 in the vicinity of the front end thereof. As illustrated in FIGS. 4 and 1, the nozzle 80 is provided with a base portion 81, a tube portion (insertion tube) 82, and a front end portion 83. The base portion 81 is a member for attaching the nozzle 80 to the front end portion 72 of the syringe 70. The tube portion 82 is inserted into the eye. The front end portion 83 is formed at the front end of the tube portion 82 and bent with respect to the tube portion 82.

As illustrated in FIG. 4, the front end portion 83 is provided with an eave 84. The eave 84 prevents the graft from rising when the fluid is discharged. Because the front end portion 83 of the nozzle 80 (tube portion 82) is bent, the nozzle 80 can be inserted under the retina in a preferred manner.

The nozzle 80 is inserted into the patient's eye. Thus, the nozzle 80 includes a material with biocompatibility. The nozzle 80 houses a graft in the front end portion 83. Thus, the nozzle 80 includes a translucent material so that the surgeon can recognize the position of the graft. The material of the nozzle 80 may include a resin such as ethylene tetrafluoroethylene or polypropylene. When the graft is colored, the surgeon can visually recognize the graft through a transparent nozzle front end. For example, the surgeon can easily recognize the position of the graft including a colored cell sheet of retinal pigment epithelial cells.

The base portion 81 has an inner diameter slightly larger than the outer diameter of the front end portion 72 so that the base portion 81 can be fitted onto the front end portion 72 of the syringe 70. The tube portion 82 has a length such that the front end portion 83 can reach the fundus when the tube portion 82 is inserted into the eye. The length of the tube portion 82 is on the order of 20 mm to 50 mm, for example. The front end portion 83 is bent such that the front end portion 83 is gently angled with respect to the fundus plane when the tube portion 82 is inserted into the eye.

The eave 84 is formed on an upper part of the front end in such a manner as to protrude from the front end (opening) of the front end portion 83 in the direction in which the front end portion 83 extends. The eave 84 prevents the rising and inversion of the graft. For this reason, the eave 84 is formed on the side of the front end portion 83 toward which the front end portion 83 is bent. The outer diameter (thickness) of the eave 84 is approximately one half the outer diameter (thickness) of the front end portion 83. When the front end portion 83 and the eave 84 are inserted under the retina (between the retina and the pigmented layer), the eave 84 is disposed on the retina side (toward which the bending is provided) so as to place the graft on the pigmented epithelium side. The length of the eave 84 in the longitudinal direction is such that the graft discharged under the eave 84 can be prevented from rotating or rising and such that the space under the retina can be prevented from being expanded excessively. For example, the length of the eave 84 is slightly greater than the length of the graft.

The tube portion 82 and the front end portion 83 have flat cross sectional shapes (in a direction perpendicular to the longitudinal direction). Thus, a sheet-shaped graft suctioned and held in the front end portion 83 can be prevented from rotating or inverting in the front end portion 83. Accordingly, it is preferable to form the tube portion 82 and the front end portion 83 with diameters (sizes) in accordance with the size of the graft. According to the present embodiment, the widths (thicknesses) of the flat shapes of the tube portion 82 and the front end portion 83 are on the order of 1 mm to 3 mm in the longer axes thereof and 0.5 mm to 1 mm in the shorter axes thereof. Because the cross sections of the tube portion 82 and the front end portion 83 are flat, the suctioned and discharged graft (cell sheet) is not easily damaged.

The nozzle 80 may have optical transparency only at a portion in which the suctioning of the graft takes place. The nozzle 80 as a whole does not need to have optical transparency. Similarly, the tube portion 82 and the front end portion 83 may have flat cross sections only at portions in which the suctioning of the graft takes place. The tube portion 82 and the front end portion 83 do not need to have flat cross sections throughout.

Figure 5A:
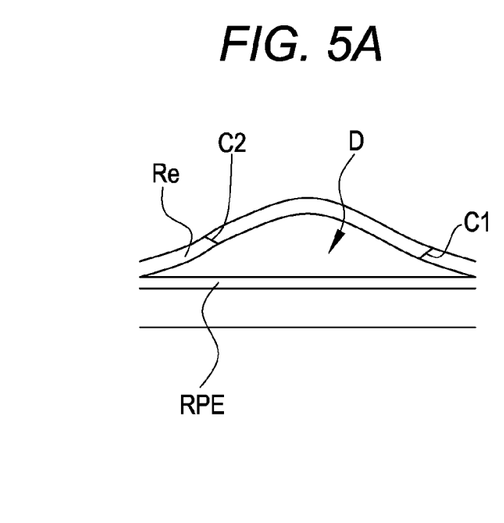
FIGS. 5A to 5C illustrate an operation for transplanting a graft.
Figure 5B:
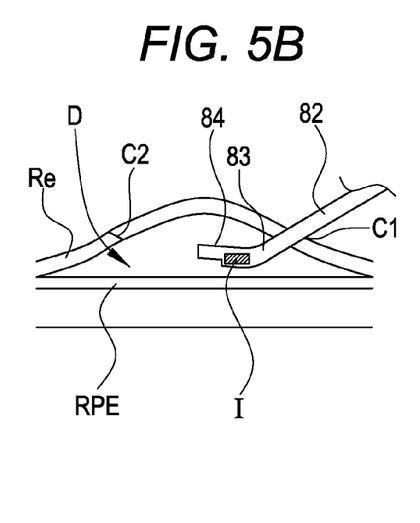
Figure 5C:
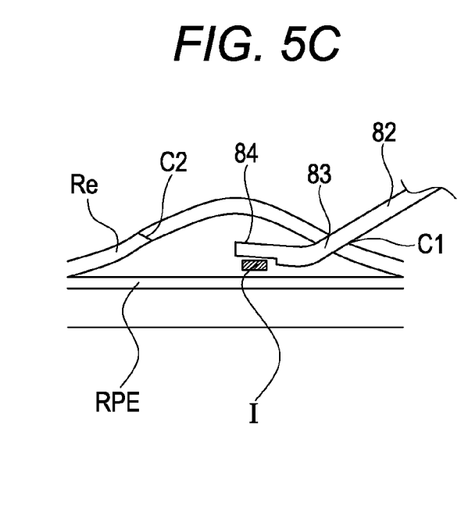

A surgery (transplant operation) utilizing the surgical instrument 100 with the above-described configuration will be described. FIGS. 5A to 5C illustrate the transplant operation utilizing the surgical instrument 100. According to the present embodiment, the graft is a sheet of cells. The cell sheet is obtained by causing a tissue harvested from a patient in advance to differentiate into retinal pigment epithelial cells, and then culturing the retinal pigment epithelial cells. The graft is cut into small pieces (such as strips measuring 1 mm×2 mm) and transplanted (placed) under the retina in the fundus of the patient's eye by using the surgical instrument 100.

The surgeon (or assistant) attaches the nozzle 80 to the syringe 70, and then inserts the syringe 70 into the pipe portion 20. When the syringe 70 inserted into the opening 21 is rotated, the flange 74 is fixed (locked) onto the fixing portion 13. The surgeon rotates the bar 32 to dispose the pressing portion 77 between the plate 33 and the rotary pin 34. When the rotary pin 34 is rotated, the pressing portion 77 is sandwiched between the plate 33 and the rotary pin 34. The surgeon, holding the grip portion 11, rotates the rotary knob 40 forward so as to move the plunger 75 forward as much as allowed. The surgeon then puts the front end portion 83 in an irrigating solution, and rotates the rotary knob 40 backward so as to move the plunger 75 backward. As a result, the tank portion T is filled with the irrigating solution. The surgeon then holds the surgical instrument 100 vertically to remove air in the nozzle 80 and the tank portion T, whereby the surgical instrument 100 is placed in a usable state (state of FIG. 2B).

The surgeon introduces the graft (tissue to be transplanted) which has been processed into a small piece in advance into the surgical instrument 100 by suction. First, the surgeon places the front end portion 83 in the vicinity of the graft placed in a Petri dish and the like. The surgeon rotates the rotary knob 40 rearward to introduce the irrigating solution into the tank portion T by suction via the front end portion 83. At the same time, the graft is suctioned into the front end portion 83. Because the front end portion 83 has a flat cross section, the cell sheet is held in the front end portion 83, together with the irrigating solution, without being inverted. Thereafter, the surgeon operates the rotary knob 40 so as to cause the cell sheet to be positioned in the vicinity of the opening (front end) of the front end portion 83.

During the transplant surgery, a perforated hole is formed in the sclera on the anterior segment of the patient's eye. Via the perforated hole, forceps and the like are inserted into the eye. As illustrated in FIG. 5A, under the retina in the fundus of the patient's eye, namely, between the retina Re and the pigmented layer RPE, a domed space D is formed.

The space D is formed by injecting the irrigating solution and the like via an incision C1 formed by incising a part of the retina Re. In the retina Re, an incision C2 different from the incision C1 is formed. The incision C1 and the incision C2 are formed opposite each other. Some of the irrigating solution and the like injected via the incision C1 into the space D flows out via the incision C2. Thus, the burden on the retina Re, such as the pressure applied to the retina Re and the like due to the irrigating solution and the like can be decreased.

Next, the surgeon removes unwanted neovascular vessels from within the dome, and then inserts the front end portion 83 with the graft I held therein into the space D, as illustrated in FIG. 5B. The surgeon then rotates the rotary knob 40 forward so as to discharge the graft I into the space D, as illustrated in FIG. 5C. The eave 84 prevents the graft I from rising or inverting when the graft I is discharged out of the opening of the front end portion 83. If the graft I is inverted or positioned erroneously, the surgeon can change the posture or position of the graft I by using the eave 84. After placing the graft I at the graft position, the surgeon pulls the front end portion 83 from the eye, and then removes the irrigating solution from within the space D by suction. Thus, the retina Re is brought back to its original state. In this way, the graft I is transplanted in the patient's eye.

As described above, in the surgery utilizing the surgical instrument 100, the graft I is moved via the fluid. In other words, the graft I is suctioned into the tube portion 82 and then discharged out of the front end portion 83. Thus, the graft is prevented from damaging. The surgical instrument 100 is operated by the surgeon rotating the operating unit (operating member), i.e., the rotary knob 40, with the finger. Accordingly, the surgical instrument 100 has high operability. Further, in the surgical instrument 100, the amount of rotation of the rotary knob 40 is translated into a reduced amount of movement of the rotary knob 40 in the front-rear direction. The amount of movement of the rotary knob 40 in the front-rear direction corresponds to the amount of movement of the plunger 75. Thus, the surgeon can easily fine-adjust the movement of the graft I (during suctioning and discharging). In other words, the surgical instrument 100 has high operability.

In the surgical instrument 100 illustrated in FIG. 1, the handpiece 10 and the syringe 70 are individual units. However, the surgical instrument 100 may include a handpiece with an integrally built tank portion in other ways. That is, the surgical instrument 100 may include a handpiece integrated with a syringe.

In the foregoing description, the syringe 70 is of disposable type. However, the surgical instrument 100 as a whole may be made of metal and the like in other ways. That is, the syringe 70 may be adapted for autoclaving and configured to be used repeatedly. The syringe 70 may include the tank portion T and be configured to change the volume of the tank portion T by the plunger 75. The syringe 70 may be of reusable type adapted for autoclaving. The volume of the syringe 70 may not be 1 mL. The volume of the syringe 70 may have a different volume in accordance with the size and the like of the graft.

In the foregoing description, the surgeon moves the pressing portion 77 in the front-rear direction so as to move the plunger 75 in the front-rear direction (axial direction of the syringe 70). However, the syringe 70 may be provided with a screw portion in threaded engagement with the plunger 75 rearwardly thereof in other ways. In this configuration, the plunger 75 is moved in the front-rear direction by rotating a screw. Specifically, the rear end of the outer cylinder 71 has a thread. The syringe 70 includes a rotary member with a thread engaging with the thread of the rear end. The rotary member is connected to the plunger 75 by being threadedly engaged with the outer cylinder 71. When the rotary member is rotated, the plunger 75 is moved in the front-rear direction in accordance with the amount of rotating movement (amount of rolling) of the rotary member. In this case, the movable unit 30 is configured to transmit the rotation of the rotary knob 40 to the rotary member.

In the foregoing description, the plunger 75 is moved in the front-rear direction. However, the plunger 75 may be configured to change the volume of the tank portion T in other ways. The plunger 75 may include a movable member that can function as a suction/discharge unit. The suction/discharge unit may include a pressure changing unit, such as a pump, for changing the volume or pressure of the inside of the tank portion T. In this case, the pump is connected to the tank portion T, for example, so that the air pressure, water pressure and the like in the tank portion T can be changed by the pump.

In the foregoing description, the rotary knob 40 is moved in the front-rear direction in accordance with the rotating movement (operation) of the rotary knob 40. However, the rotary knob 40 may be configured to axially rotate without linear motion in other ways. In this case, the rotary knob 40 functions as a gear and pulley to move another member, such as the slider 30B. In this case, the operating member provides a pinion and the slider 30B (or a part thereof) provides a rack.

In the foregoing description, the movable unit 30 is moved in the front-rear direction by rotating the rotary knob 40. However, the operating member of the surgical instrument 100 may have the function of transmitting an operation by the surgeon to the suction/discharge unit (plunger 75) via rotation in other ways. The operating member may be configured to move on the grip portion in one direction (such as in the front-rear direction).

In the foregoing description, the amount of movement of the suction/discharge unit (plunger 75) is set by reducing the amount of operation (amount of rotation) of the operating member (rotary knob 40) via the moving mechanism (movable unit 30). However, the moving mechanism may be configured to directly equate the amount of operation of the operating member with the amount of movement of the suction/discharge unit in other ways.

In the foregoing description, the rotation of the rotary knob 40 as the operating member (operating unit) is translated into the movement in the front-rear direction, whereby the plunger 75 is moved in the front-rear direction. However, the surgical instrument 100 may be configured such that the fluid can be suctioned and discharged via the nozzle 80 in accordance with the operation of the operating unit in other ways. For example, the operating unit is a signal input unit, such as a switch. In this case, the movement of the plunger 75 may be caused by an actuator and the like driven on the basis of a signal outputted from the switch.

In the foregoing description, the nozzle 80 has the eave 84 at the front end portion 83. However, the front end portion 83 may not include the eave 84. The nozzle 80 (front end portion 83) may be configured to simply suction and discharge a graft.

In the foregoing description, a cell sheet of retinal pigment cells has been described as an example of the graft (biological tissue). However, the graft may be other eye tissues (biological tissues), such as a cornea cell sheet.

The present medical instrument may be used for other ophthalmic surgery or diagnosis. The present medical instrument may be used for intravitreal injection (administration), or for harvesting anterior chamber fluid. The present medical instrument may be preferably used for cell sheet transplantation because of its decreased likelihood for inflicting damage. The present medical instrument may be preferably used for ophthalmic surgery because the instrument enables operation in a very small space.

The present medical instrument may be applied for purposes other than ophthalmology. In other words, the present medical instrument may be used for surgery or diagnosis of other biological tissues or organs. The present medical instrument may be applied for any and every purpose involving the function for suctioning and/or discharging (injecting) an object. For example, the present medical instrument can be used for sample administration (such as transplantation or administration of a drug) or sample harvesting (such as blood sampling or tissue harvesting). The object that is suctioned and/or discharged may be in the form of liquid, solid, or gel, or in capsule or sheet form. The type of the object may include a graft, a cell suspension, a drug (such as a drug releasing capsule or sheet), and a biological sample. The present medical instrument may be used for animals other than humans.

The present disclosure is not limited to the embodiment and may include various modifications. The present disclosure includes the modifications within the technical scope of the disclosure.

At the rear end portion of the outer cylinder 71, a pair of flanges (collar portions) 74 may be provided. The eave 84 may be formed across one half the outer diameter of the front end portion 83 in a cross section thereof. The surgical instrument 100 may be configured such that the rotary knob 40 is rotated and the rotary knob 40 is linearly moved in accordance with the amount of the rotating movement (operation amount).

The medical instrument according to the present embodiment may include the following first to sixteenth medical instruments. A first medical instrument is a medical instrument provided with a handpiece to be held by a surgeon and is manually operated by the surgeon. The first medical instrument is provided with: a tank portion configured to house a predetermined fluid; a suction/discharge unit for changing a volume or pressure of an inside of the tank to suction a fluid into the tank portion or discharge the fluid from the tank portion; and an operating unit that is a member different from the suction/discharge unit and connected to the suction/discharge unit for operating the suction/discharge unit.

A second medical instrument is based on the first medical instrument, wherein the suction/discharge unit is a plunger fitted to the tank portion and configured to be moved forward and backward along an axial direction of the tank portion so as to change the volume in the tank portion. A third medical instrument is based on the second medical instrument, wherein the operating unit includes a moving mechanism that holds the suction/discharge unit and moves the suction/discharge unit along an axial direction of the handpiece.

A fourth medical instrument is based on the third medical instrument, wherein the moving mechanism is provided with: a holder holding the suction/discharge unit; a movable member that axially moves the holder along a guide portion provided along an axial direction of the handpiece which is different from the axis of the suction/discharge unit; and a rotary member joined to the movable member and rotated along the guide portion while in contact with the guide portion.

A fifth medical instrument is based on the fourth medical instrument, wherein the rotary member is a rotary knob operated by a surgeon, a predetermined portion of the rotary knob with a diameter smaller than a maximum outer diameter of the rotary knob contacting the guide portion.

A sixth medical instrument is based on the second medical instrument, wherein the tank portion and the suction/discharge unit form a syringe. A seventh medical instrument is based on the sixth medical instrument, wherein the handpiece is provided with an attaching/detaching member configured to detachably attach the tank portion.

An eighth medical instrument is based on the first medical instrument, comprising a nozzle connected to the tank portion and providing a channel for suctioning the fluid into the tank portion or discharging the fluid out of the tank portion, wherein at least a front end portion of the nozzle is formed from a material with optical transparency.

A ninth medical instrument is based on the eighth medical instrument, wherein the nozzle has a flat cross sectional shape in at least the front end portion thereof. A tenth medical instrument is based on the ninth medical instrument, wherein the nozzle includes an eave protruding forward from an upper end of the front end of the nozzle relative to a lower end of the front end. An eleventh medical instrument is based on the eighth medical instrument, wherein a biological tissue is placed in the nozzle together with the fluid, wherein the biological tissue is discharged out of the nozzle together with the fluid. A twelfth medical instrument is based on the eleventh medical instrument, wherein the biological tissue is a tissue to be transplanted.

A thirteenth medical instrument is based on the eleventh medical instrument, wherein the biological tissue is a sheet-like tissue. A fourteenth medical instrument is based on the first medical instrument, wherein the operating unit has at least a portion thereof disposed over the handpiece.

A fifteenth medical instrument is a medical instrument provided with a handpiece to be held by a surgeon and is manually operated by the surgeon, the medical instrument provided with: an attaching/detaching member configured to detachably attach a tank portion configured to house a predetermined fluid to a handpiece; and an operating unit including a movable mechanism for detachably holding a suction/discharge unit for suctioning the fluid into the tank portion attached to the attaching/detaching member or discharging the fluid from the tank portion and for moving the suction/discharge unit along an axial direction of the handpiece. A sixteenth medical instrument is based on the fifteenth medical instrument, wherein the tank portion and the suction/discharge unit form a syringe.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A medical instrument comprising:
   a handpiece comprising an opening at a front end of the handpiece, a grip portion that forms an outer cylinder of the handpiece, and a fixing portion at a rear end of the handpiece, the opening, the outer cylinder, and the fixing portion being coaxial with each other;
   a syringe in the handpiece held by the fixing portion of the handpiece, the syringe comprising a front end portion that is inserted in the opening of the handpiece, a tank portion configured to house a fluid, and a plunger that changes a volume or pressure of an inside of the tank portion to at least one of suction the fluid into the tank portion and discharge the fluid from the tank portion; and an operating unit providing a member different from the plunger and configured to operate the plunger, the operating unit being disposed on a side of the outer cylinder of the grip portion and between the opening of the handpiece and the fixing portion of the handpiece, wherein the operating unit comprises a moving mechanism for moving the plunger along an axis of the outer cylinder of the handpiece, the moving mechanism comprising:
a holder holding the plunger,
a guide portion extending parallel to the axis of the outer cylinder of the handpiece,
an operation member disposed on a side of the outer cylinder of the grip portion and configured to move along a longitudinal axis of the guide portion while in contact with the guide portion, and
a movable member configured to move the holder along the longitudinal axis of the guide portion in accordance with the movement of the operation member; and
the longitudinal axis of the guide portion is different from a longitudinal axis of the plunger,
wherein the outer cylinder comprises a groove extending parallel to an axis of the outer cylinder, the groove being formed on an outer surface of the outer cylinder and between the opening and fixing portion of the handpiece, and
the operation member is a rotary disc disposed in the groove of the outer cylinder.

2. The medical instrument according to claim 1, wherein the plunger is configured to be moved in the tank portion along an axial direction of the tank portion.

3. The medical instrument according to claim 1, wherein the operating unit includes the rotary disc for moving the plunger along the axis of the outer cylinder of the handpiece, the rotary disc is configured to move along the longitudinal axis of the guide portion while in contact with the guide portion, a rotation axis of the rotary disc is perpendicular to the longitudinal axis of the guide portion and the longitudinal axis of the plunger.

4. The medical instrument according to claim 3, wherein:
the rotary disc is a rotary knob operated by a surgeon; and
the rotary knob includes a portion contacting the guide portion, the portion having a diameter smaller than a maximum diameter of the rotary knob.

5. The medical instrument according to claim 2, further comprising a syringe,
wherein the syringe includes the tank portion and the plunger.

6. The medical instrument according to claim 5, wherein the handpiece includes an attaching and detaching member configured to detachably attach the syringe to the handpiece.

7. The medical instrument according to claim 1, further comprising a nozzle connected to the tank portion and providing a channel for suctioning the fluid into the tank portion or discharging the fluid from the tank portion,
wherein the nozzle has optical transparency in at least a part of a front end portion thereof.

8. The medical instrument according to claim 1, further comprising a nozzle connected to the tank portion and providing a channel for suctioning the fluid into the tank portion or discharging the fluid from the tank portion, wherein the at least a part of the front end portion of the nozzle has a flat cross sectional shape in a direction perpendicular to a longitudinal direction of the nozzle.

9. The medical instrument according to claim 8, wherein the front end portion of the nozzle has an eave extending in a direction in which the front end portion of the nozzle extends.

10. The medical instrument according to claim 7, wherein the fluid includes a biological tissue.

11. The medical instrument according to claim 10, wherein the biological tissue is a tissue to be transplanted.

12. The medical instrument according to claim 10, wherein the biological tissue is a sheet-like tissue.

13. The medical instrument according to claim 1, further comprising a nozzle connected to the tank portion and providing a channel for suctioning the fluid into the tank portion or discharging the fluid from the tank portion,
wherein an axis of the nozzle is coaxial with the axis of the outer cylinder of the handpiece.

14. The medical instrument according to claim 13, wherein the nozzle is disposed at the front end of the handpiece, and the operation member is disposed closer to the front end of the handpiece than a center of the handpiece in a direction of the axis of the outer cylinder.

15. A medical instrument comprising:
a handpiece comprising an opening at a front end of the handpiece, a grip portion that forms an outer cylinder of the handpiece, and a fixing portion at a rear end of the handpiece, the opening, the outer cylinder, and the fixing portion being coaxial with each other;
a syringe detachably attached in the handpiece by the fixing portion of the handpiece;
an attaching and detaching member configured to detachably attach the syringe to the handpiece; and
an operating unit configured to operate the plunger, wherein
the syringe comprises a front end portion that is inserted in the opening of the handpiece, a tank portion configured to house a fluid, and a plunger for at least one of suctioning the fluid into the tank portion and discharging the fluid from the tank portion, and
the operation unit comprises a moving mechanism for moving the plunger along an axis of the outer cylinder of the handpiece, the operating unit being disposed on a side of the outer cylinder of the grip portion and between the opening of the handpiece and the fixing portion of the handpiece; and
the moving mechanism comprises:
a holder holding the plunger;
a guide portion extending parallel to the axis of the outer cylinder of the handpiece;
a rotary member disposed on a side of the outer cylinder of the grip portion and configured to rotate along a longitudinal axis of the guide portion while in contact with the guide portion; and
a movable member configured to move the holder along the longitudinal axis of the guide portion in accordance with the rotating movement of the rotary member,
the longitudinal axis of the guide portion being different from a longitudinal axis of the plunger, and
a rotation axis of the rotary member being perpendicular to the longitudinal axis of the guide portion and the longitudinal axis of the plunger,
wherein the outer cylinder comprises a groove extending parallel to an axis of the outer cylinder, the groove being formed on an outer surface of the outer cylinder and between the opening and fixing portion of the handpiece, and
the rotary member is a rotary disc disposed in the groove of the outer cylinder.

16. The medical instrument according to claim 15, further comprising a nozzle connected to the tank portion and providing a channel for suctioning the fluid into the tank portion or discharging the fluid from the tank portion,
   wherein an axis of the nozzle is coaxial with the axis of the outer cylinder of the handpiece.

17. The medical instrument according to claim 16, wherein the nozzle is disposed at the front end of the handpiece, and the rotary member is disposed closer to the front end of the
   handpiece than a center of the handpiece in a direction of the axis of the outer cylinder.

18. The medical instrument according to claim 15, wherein an amount of movement of the movable member is proportional to an amount of rotation of the rotary disc.

* * * * *